(12) United States Patent
Stewart et al.

(10) Patent No.: US 11,457,976 B2
(45) Date of Patent: Oct. 4, 2022

(54) DIRECTIONALLY FOCUSED ABLATION DEVICE

(71) Applicant: Medtronic, Inc., Minneapolis, MN (US)

(72) Inventors: Mark T. Stewart, Lino Lakes, MN (US); Brian T. Howard, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 747 days.

(21) Appl. No.: 16/242,081

(22) Filed: Jan. 8, 2019

(65) Prior Publication Data

US 2019/0209235 A1     Jul. 11, 2019

Related U.S. Application Data

(60) Provisional application No. 62/615,608, filed on Jan. 10, 2018.

(51) Int. Cl.
*A61B 18/14*     (2006.01)
*A61B 5/0538*     (2021.01)
(Continued)

(52) U.S. Cl.
CPC ........ *A61B 18/1492* (2013.01); *A61B 5/0538* (2013.01); *A61B 5/282* (2021.01);
(Continued)

(58) Field of Classification Search
CPC .............. A61M 25/10; A61M 25/1002; A61M 25/1011; A61M 25/10181;
(Continued)

(56) References Cited

U.S. PATENT DOCUMENTS

| 2002/0091427 A1 | 7/2002 | Rappaport et al. |
| 2004/0087935 A1 | 5/2004 | Taimisto et al. |

(Continued)

FOREIGN PATENT DOCUMENTS

| WO | 2006138461 A2 | 12/2006 |
| WO | 2010056745 A1 | 5/2010 |
| WO | 2015171921 A2 | 11/2015 |

OTHER PUBLICATIONS

International Search Report and Written Opinion dated Apr. 12, 2019, for corresponding International Application No. PCT/US2019/012631 International Filing Date: Jan. 8, 2019 consisting of 13 pages.

*Primary Examiner* — Thomas A Giuliani
*Assistant Examiner* — Christine A Dedoulis
(74) *Attorney, Agent, or Firm* — Michael Best & Friedrich LLP

(57) ABSTRACT

A medical device for directionally focusing energy to a treatment site, the medical device including a shaft having an elongated body defining a proximal portion and a distal portion opposite the proximal portion, the distal portion including at least one electrode having a contact portion and a permeable sheath at least partially surrounding the at least one electrode, the permeable sheath and the at least one electrode defining an insulation cavity, the permeable sheath being impermeable to an insulation material introduced to the insulation cavity from a fluid source configured to be coupled to the shaft.

19 Claims, 5 Drawing Sheets

(51) Int. Cl.
*A61B 18/12* (2006.01)
*A61B 18/00* (2006.01)
*A61B 17/00* (2006.01)
*A61B 5/282* (2021.01)

(52) U.S. Cl.
CPC .................. *A61B 18/1206* (2013.01); *A61B 2017/00154* (2013.01); *A61B 2018/0016* (2013.01); *A61B 2018/00023* (2013.01); *A61B 2018/00083* (2013.01); *A61B 2018/00107* (2013.01); *A61B 2018/00136* (2013.01); *A61B 2018/00351* (2013.01); *A61B 2018/00357* (2013.01); *A61B 2018/00577* (2013.01); *A61B 2018/00839* (2013.01); *A61B 2018/00892* (2013.01); *A61B 2018/1465* (2013.01); *A61B 2018/1497* (2013.01)

(58) Field of Classification Search
CPC .......... A61M 2025/09008; A61M 2025/1086; A61F 7/123; A61B 2017/3486
See application file for complete search history.

(56) References Cited

U.S. PATENT DOCUMENTS

| | | | |
|---|---|---|---|
| 2011/0190751 A1* | 8/2011 | Ingle | A61B 18/02 606/21 |
| 2012/0029511 A1* | 2/2012 | Smith | A61B 18/1492 606/41 |
| 2013/0324987 A1 | 12/2013 | Leung et al. | |
| 2014/0378962 A1 | 12/2014 | Anderson et al. | |
| 2016/0278839 A1* | 9/2016 | Pedersen | A61B 18/1492 |
| 2017/0157394 A1* | 6/2017 | Andocs | A61B 18/14 |

* cited by examiner

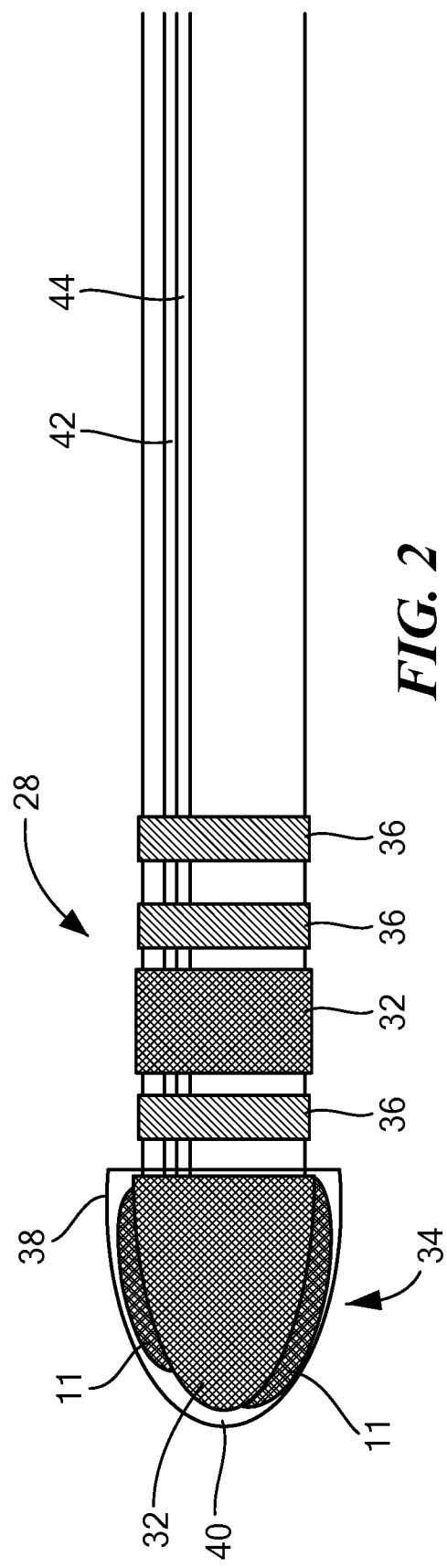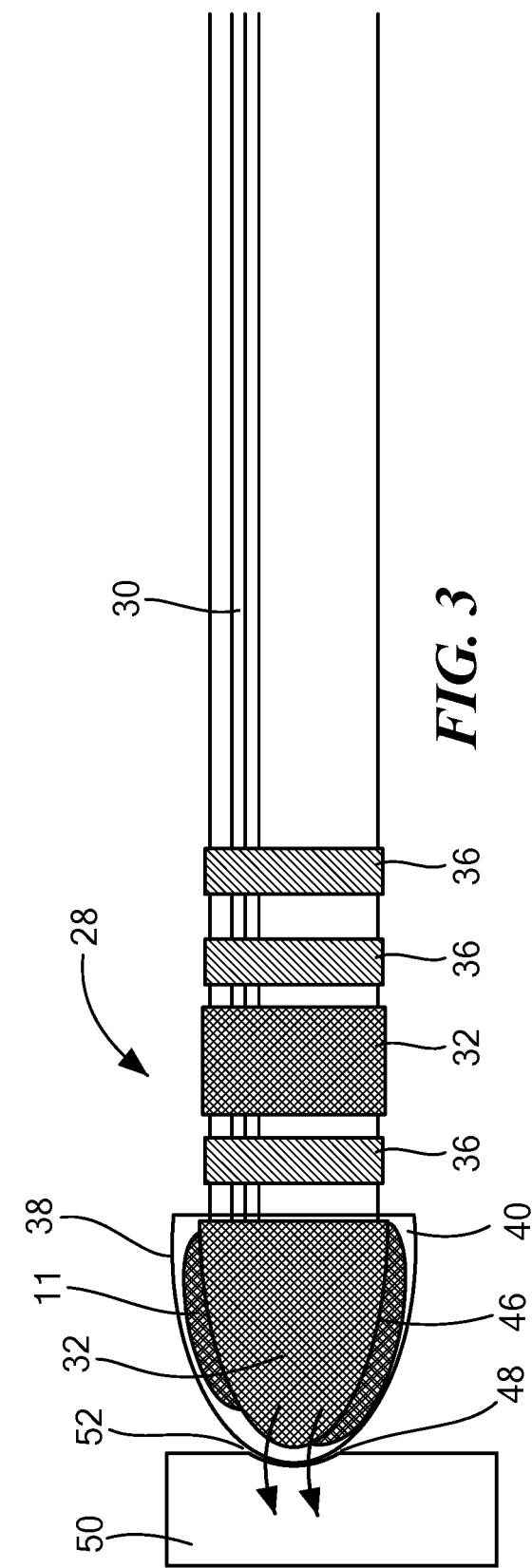

DIRECTIONALLY FOCUSED ABLATION DEVICE

CROSS-REFERENCE TO RELATED APPLICATION

This application claims the benefit of U.S. Application Ser. No. 62/615,608, filed Jan. 10, 2018.

FIELD

The present technology is generally related to ablation, and more particularly, to a device, system, and method for ablating cardiac tissue using directionally focused non-thermal energy.

BACKGROUND

Tissue ablation is a medical procedure commonly used to treat conditions, such as cardiac arrhythmia, which includes atrial fibrillation. Ablation may be performed to modify tissue by stopping aberrant electrical propagation and/or disrupting aberrant electrical conduction through cardiac muscle tissue. Thermal ablation techniques, such as cryoablation and radiofrequency (RF) ablation, are frequently used, however such techniques are time consuming and carry a risk of complications. For example, because thermal ablation techniques require relatively high amounts of energy, such energy increases the risk of tissue damage. As such, non-thermal techniques, such as pulsed field ablation (PFA) may also be used. PFA involves the application of short pulsed electric fields (PEF) which may reversibly or irreversibly destabilize cell membranes through electropermeabilization without generally affecting the structural integrity of the tissue components, including the acellular cardiac extracellular matrix. The nature of PFA allows for very brief periods of therapeutic energy delivery, on the order of tens of milliseconds in duration. However, when not directionally controlled, PFA will deliver energy into, for example, the blood, which is not intended for ablation and where that portion of the electric current is wasted. In some cases, such non-directionally controlled energy may cause collateral damage to non-target tissue, although not as frequently or as severely as thermal ablation techniques.

SUMMARY

The techniques of this disclosure generally relate to ablating cardiac tissue.

In one embodiment, a medical device for directionally focusing energy to a treatment site comprises: a shaft having an elongated body defining a proximal portion and a distal portion opposite the proximal portion, the distal portion including at least one electrode having a contact portion; and a permeable sheath at least partially surrounding the at least one electrode, the permeable sheath being impermeable to an insulation material, the permeable sheath and the at least one electrode defining an insulation cavity therebetween.

In one aspect of the embodiment, the permeable sheath is composed of a hydrophilic permeable membrane and the insulation material is at least one of a gas and a hydrophobic material such that the insulation material is retained within the hydrophilic permeable membrane.

In one aspect of the embodiment, the insulation material is introduced into the insulation cavity from a fluid source configured to be coupled to the shaft, the insulation cavity being configured to retain the insulation material when the insulation material is introduced into the insulation cavity from the fluid source.

In one aspect of the embodiment, the insulation material is a displaceable solid material. In one aspect of the embodiment, the displaceable solid material is at least one of granular particles, microspheres, ceramic microspheres, polymeric microspheres, and hydrophobic polymeric microspheres, the insulation cavity containing a predetermined amount of the insulation material.

In one aspect of the embodiment, the permeable sheath is configured to cause energy to flow from the contact portion of the at least one electrode.

In one aspect of the embodiment, the medical device further comprises a second electrode positioned proximally on the shaft relative to the at least one electrode, the at least one electrode including a conductive surface area smaller than a conductive surface area of the second electrode.

In one aspect of the embodiment, the medical device further comprises a second electrode proximate the at least one electrode and an impermeable membrane disposed between and electrically isolating the at least one electrode and the second electrode from each other.

In one aspect of the embodiment, the medical device further comprises a flexible member at least partially defining a circular shape of the distal portion of the elongated body of the shaft, and a second electrode disposed on the distal portion proximate the at least one electrode, the at least one electrode being an energy delivery electrode and the second electrode being a diagnostic electrode.

In one aspect of the embodiment, the medical device further comprises a second electrode proximate the at least one electrode, and a separation element disposed between the at least one electrode and the second electrode, the separation element defining a separation distance between a first electric field delivered by the at least one electrode and a second electric field delivered by the second electrode.

In one embodiment, a medical system for directionally focusing energy to a treatment site comprises: a medical device including: a shaft including an elongated body defining a proximal portion and a distal portion opposite the proximal portion, the shaft including one or more electrodes; a permeable sheath at least partially surrounding at least one of the electrodes, the permeable sheath being permeable to a pulsed electric field and impermeable to an insulation material, the permeable sheath and the at least one of the plurality of electrodes defining an insulation cavity therebetween for enclosing the insulation material; a fluid source coupled to the medical device, the fluid source being configured to introduce the insulation material into the insulation cavity; and an energy source coupled to the medical device, the energy source being configured to transmit the pulsed electric field to the at least one electrode.

In one aspect of the embodiment, each of the plurality of electrodes defines an outer surface, and the insulation material is configured to translate from a first position on the outer surface to a second position on the outer surface when the permeable sheath is in contact with the treatment site.

In one aspect of the embodiment, each of the plurality of electrodes includes a first electrode at the distal portion of the shaft and a second electrode positioned proximally on the shaft relative to the first electrode, the first electrode including a conductive surface area smaller than a conductive surface area of the second electrode.

In one aspect of the embodiment, each of the plurality of electrodes includes a first electrode and a second electrode proximate the first electrode and an impermeable membrane disposed between and electrically isolating the first electrode and the second electrode from each other.

In one aspect of the embodiment, the medical device includes a flexible member at least partially defining a circular shape of the distal portion of the shaft, the distal portion of the shaft including a first electrode and a second electrode of the electrodes disposed thereon, the first electrode being an energy delivery electrode and the second electrode being a diagnostic electrode.

In one aspect of the embodiment, the present disclosure provides the medical system including a separation element disposed between the electrodes, the separation element defining a separation distance between a first electric field and a second electric field delivered by the electrodes.

In one aspect of the embodiment, the medical device further includes a fluid delivery lumen in fluid communication with the fluid source and the insulation cavity.

In one aspect of the embodiment, the medical system further comprises a fluid circuit in communication with the insulation cavity, the fluid circuit including a fluid delivery lumen and a fluid extraction lumen.

In one embodiment, a method of directionally focusing energy to a treatment site comprises: positioning a distal portion of a medical device adjacent a tissue of a patient, the distal portion including at least one electrode at least partially surrounded by a permeable sheath, the at least one electrode and the permeable sheath defining an insulation cavity, and the permeable sheath being permeable to a pulsed electric field and impermeable to an insulation material; actuating a fluid source to deliver the insulation material from the fluid source to the insulation cavity of the medical device, the insulation material configured to be disposed within the insulation cavity; and actuating an energy source to deliver a pulsed field of energy from the energy source to the distal portion of the at least one electrode.

In one aspect of the embodiment, the method further comprises adjusting an amount of the insulation material within the insulation cavity.

In one aspect of the embodiment, the method further comprises positioning the distal portion of the medical device in contact with the tissue.

In one aspect of the embodiment, the method further comprises positioning the distal portion of the medical device in contact with the tissue to transition the insulation material from a first portion of the at least one electrode to a second portion of the at least one electrode.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 is a close-up side view that illustrates the electrode of FIG. 1 at least partially surrounded by the permeable sheath;

FIG. 3 is a close-up side view that illustrates the electrode of FIG. 1 disposed proximate to a treatment site;

DETAILED DESCRIPTION

Figure 1:
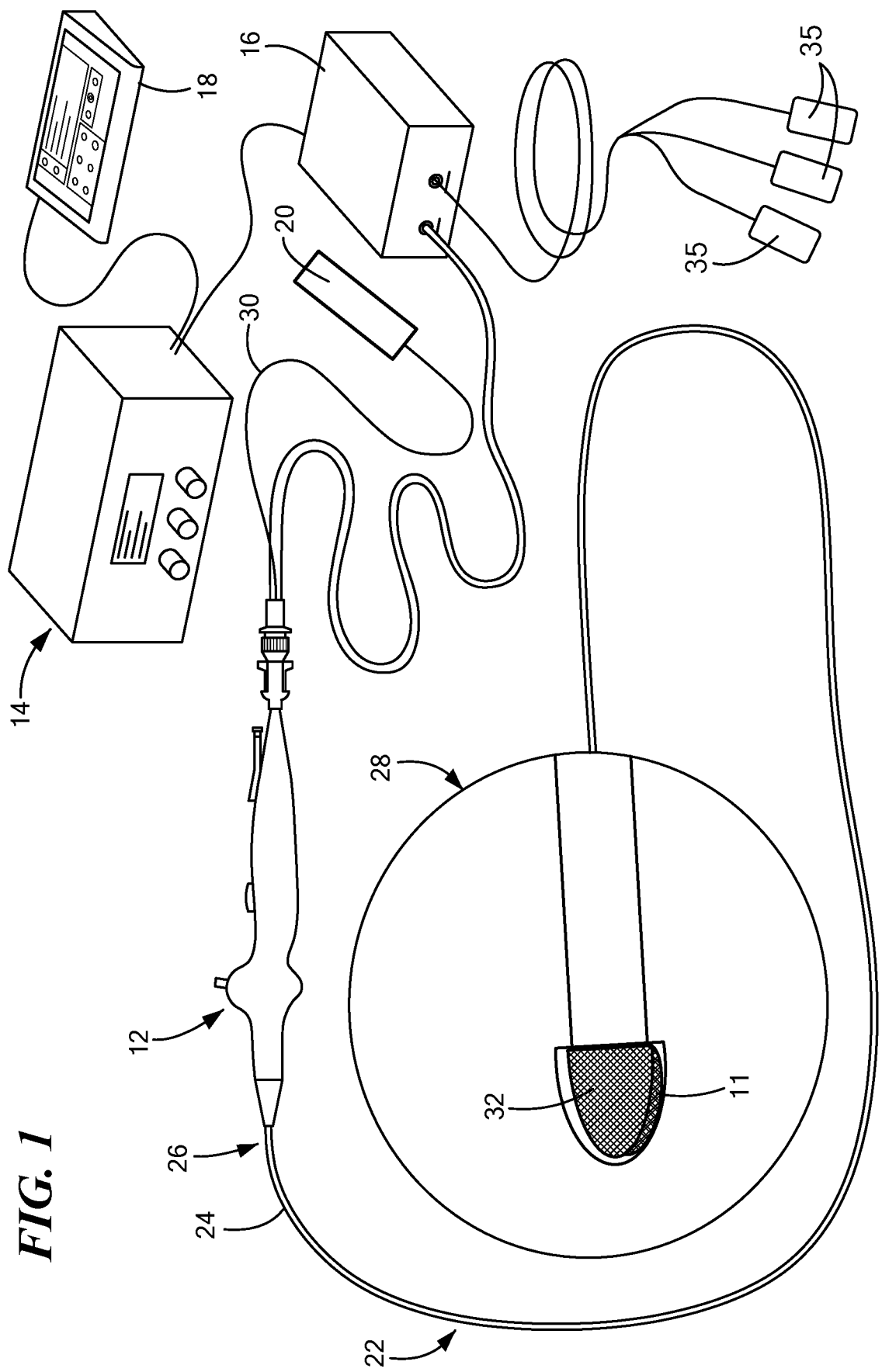
FIG. 1 is a perspective view that illustrates an exemplary medical system including a medical device having a shaft including one or more electrodes at least partially surrounded by a permeable sheath.

Before describing in detail exemplary embodiments, it is noted that the embodiments reside primarily in combinations of device, system, and method steps related to directionally focusing non-thermal energy to ablate cardiac muscle tissue. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to the drawing figures in which like reference designations refer to like elements, an embodiment of a medical system for directing energy to a tissue constructed in accordance with principles of the present invention is shown in FIG. 1 and generally designated as "10." The system 10 generally includes a medical device 12 coupled to an energy source, for example, a pulsed field ablation generator 14 including an energy control, delivering, and monitoring system. In another configuration, the medical device 12 may be coupled to an electrode distribution system 16, such as through a catheter. A remote controller 18 may further be included in communication with the generator 14 for operating and controlling the various functions of the generator 14. The system 10 may also include a source of insulation material 20. In one embodiment, the source of insulation material 20 is a fluid source, for example, a syringe, for delivering or introducing an insulation material, generally designated as "11," to the medical device 12, which may be a gas, air, carbon dioxide, or the like. Additionally or alternatively, the material may be composed of a displaceable solid, such as granular particles, microspheres, ceramic microspheres, polymeric microspheres (for example, microspheres composed of a polymer such as polytetrafluoroethylene, or PTFE), hydrophobic polymeric microspheres, or the insulation material may be a fluid or semi-fluid material, such as a liquid, gel, etc.

The medical device 12 may generally include one or more diagnostic or treatment regions for energetic, therapeutic and/or investigatory interaction between the medical device 12 and a treatment site, such as a patient's cardiac muscle tissue. The treatment regions may deliver, for example, pulsed electroporation energy, i.e., a pulsed electrical field to a tissue area in proximity to the treatment regions. The medical device 12 may include a shaft 22 having an elongate body 24 passable through a patient's vasculature and/or otherwise configured to be implanted within the patient proximate to the treatment site for diagnosis and/or treatment. The medical device 12 may be positioned within the patient using conventional steering methods, such methods involving a catheter, sheath, or intravascular introducer.

In one configuration, the elongate body 24 defines a proximal portion 26 and a distal portion 28 opposite the proximal portion 26. One or more lumens 30 may be disposed within the shaft 22 to provide mechanical, electrical, and/or fluid communication between the proximal portion 26 and the distal portion 28 of the shaft 22. The distal portion 28 of the shaft 22 may generally define the treatment regions of the medical device 12 that are operable to monitor, diagnose, and/or treat the tissue, such as through delivering the pulsed electric field from one or more electrodes 32 at the distal portion 28 of the shaft 22. The electrodes 32 may be coupled to, disposed on, or integrated within the distal portion 28 of the shaft 22 and arranged in a unipolar or bipolar configuration, depending upon the energy vectoring scheme utilized by the medical system 10.

FIG. 2 is a close-up side view of the electrode 32 disposed on the distal portion 28 of the shaft 22, such as on a distal-most end 34 of the shaft 22. In one configuration, the electrode 32 may be a unipolar electrode configured to interact with a ground/energy return electrode 35 located remotely from the medical device 12. One or more diagnostic electrodes 36 may be disposed proximally on the shaft 22 relative to the electrode 32 for performing various diagnostic functions. In one configuration, the diagnostic electrodes 36 may be positioned at least ten centimeters from the electrode 32, however other configurations are contemplated. A second electrode 32 may be positioned proximally on the shaft 22 relative to the electrode 32 with the electrode 32 including a conductive surface area smaller than a conductive surface area of the second electrode 32 (not shown).

In one configuration, a permeable sheath 38 at least partially surrounds the electrode 32 that is permeable to the pulsed electric field but impermeable to the insulation material 11. Prior to actuating the pulsed electrical field, the permeable sheath 38 may be injected with a saline to increase a diameter of the permeable sheath 38 to a size larger than a diameter of the electrode 32. Thereafter, the insulation material 11 may be introduced within an insulation cavity 40 defined by an interior region of the permeable sheath 38 and/or an area between the permeable sheath 38 and the electrode 32. The permeable sheath 38 is configured to trap the insulation material 11 within the insulation cavity 40, thereby insulating at least a portion of the electrode 32 from the pulsed electric field. In one exemplary configuration, the insulation material 11 may be in the form of a bubble that consumes approximately half of a volume of the insulation cavity 40, although more or less of the insulation cavity 40 may be occupied by the insulation material 11. As such, the insulation material 11 may be transitioned to various locations within the insulation cavity 40.

In one configuration, the insulation material 11 may be delivered to the permeable sheath 38 through a fluid delivery lumen 42 within the shaft 22 that is coupled to the source of insulation material 20. In another configuration, in addition to the fluid delivery lumen 42, a fluid extraction lumen 44 may be disposed within the shaft 22 for extracting the insulation material 11 from the insulation cavity 40 to adjust an amount of the insulation material 11 present in the insulation cavity 40 and/or to add or replace the material 11 present in the insulation cavity 40 with an additional or new insulation material. The fluid delivery lumen 42 and the fluid extraction lumen 44 may create a fluid circuit within the shaft 22. Further, as shown in exemplary FIG. 5, one or more configurations may include multiple segments having separate permeable sheaths 38. In such configurations, the lumens 30, 42, 44 may be configured to deliver and/or withdraw the insulation material 11 to one or more of the individual segments concurrently or in parallel. In other words, the lumens 30 may be coupled to one or more individual segments within the shaft 22. For example, a single lumen pair 42, 44 may provide insulation material 11 to and from the permeable sheaths 38 of the electrodes 32, while individual delivery lumens 42 coupled to the remaining segments may share a common fluid extraction lumen 44. In one or more configurations, such as the configuration of FIG. 5, an impedance meter (not shown) may be included which is configured to perform one or more functions, such as promoting a common electrical path. For example, if all of the ground/energy return electrodes 35 in the bipolar configuration were located remote from the treatment site and commonly supplied, the pulsed electrical field, i.e., therapy may not have an effective return path if all of the electrodes 32 in the shaft 22 were encompassed by the insulation material 11. As such, the ability to remove, change, and/or limit the size, quantity, presence, etc., of the insulation material 11 may promote the existence of the common electrical path.

In another configuration, the medical device 12 may be passive in that conductive aqueous fluid from the blood stream may be absorbed by the hydrophilic permeable sheath 38 which may also include a porous wall that allows the fluid to be dispersed through the wall.

Figure 4:
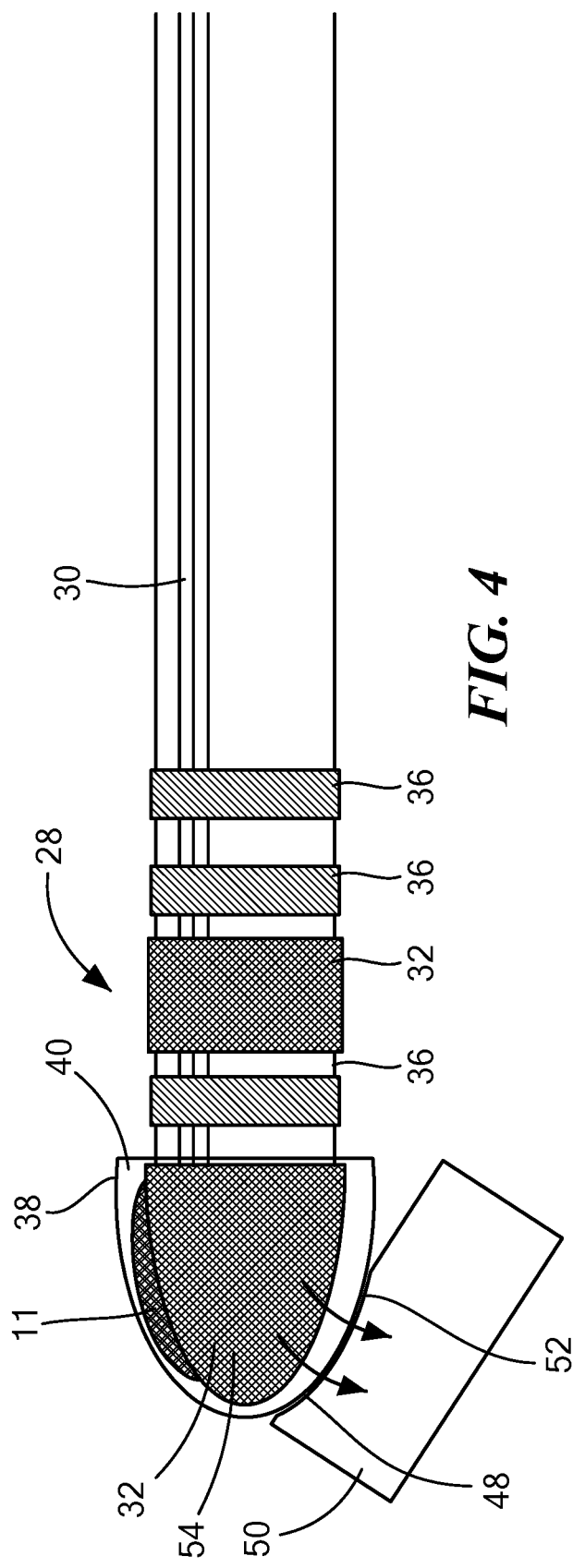
FIG. 4 is a close-up side view that illustrates the electrode of FIG. 1 disposed proximate to a treatment site different than the treatment site of FIG. 3.

FIGS. 3 and 4 are close-up side views of the electrode 32 defining an outer surface 46 having a contact portion 48 configured to be disposed adjacent to a treatment site 50, such as a portion of cardiac muscle tissue which may benefit from the pulsed electric field. When directionally focusing the pulsed electric field to a focal area 52 of the treatment site 50, the distal portion 28 of the shaft 22 may be positioned adjacent to the treatment site 50 with the contact portion 48 of the electrode 32 facing the focal area 52. In one configuration, the structure of the electrode 32 and the permeable sheath 38 are configured to cause the distal portion 28 of the shaft 22 to conform relatively easily to the anatomy of the treatment site 50, thereby assisting with facing the focal area 52 towards the treatment site 50 and not the blood. An exemplary saline which may be used to be used to at least partially fill the insulation 40 cavity inside the permeable sheath 38 is hypertonic saline, such as a solution of 2-7% saline by weight. Such saline, which is a relatively high conductivity fluid, may imbibe into the permeable sheath 38 to promote a low impedance path through the focal area 52 and into the treatment site 50. It will be understood that the electrode 32 may be at a location along the shaft 22 other than that shown in the figures, such as at a location that is a greater distance proximal from the distal-most end 34 of the shaft 22. Additionally, the electrode (s) 32 may have a larger surface area than shown in the figures. For example, each electrode 32 may be larger than shown or may include a plurality of smaller electrodes that are electrically connected to each other and function as a single larger electrode.

When the distal portion 28 of the shaft 22 contacts the treatment site 50, the material forming the electrode 32 may force the insulation material 11 from the contact portion 48 of the electrode 32 to a non-contact portion 54 of the electrode 32, thereby electrically insulating the non-contact portion 54. In other words, the insulation material 11 translates from a first position in which the insulation material 11 faces the focal area 52 to a second position in which the insulation material 11 is moved around the outer surface 46 of the electrode 32 to no longer face the focal area 52. In order to reduce the risk of buoyant forces becoming dominant, the permeable sheath 38 may be sized to allow for a relatively small amount of occupying space for the insulation material 11, which may be in the form of the bubble within a fluid. In another embodiment, the insulation material 11 may be a displaceable solid material, such as granular particles, microspheres, ceramic microspheres, polymeric microspheres, hydrophobic polymeric microspheres, or the like. During use as described herein, the displaceable solid insulation material 11 may be moved within the insulation cavity 40 as would an insulation material 11 such as bubble (s) within a fluid. Further, a predetermined quantity, volume, or amount of an insulation material 11 such as a displaceable solid material may be placed within (or "preloaded") the insulation cavity 40, such as during manufacture or assembly or before a medical procedure begins, without the need to transport the insulation material 11 through a delivery lumen. In other words, the insulation cavity 40 may provide enough space for the insulation material 11 to insulate the electrode 32 that faces the blood without allowing the insulation material 11 to easily move and amass in a direction that is upward relative to the position of the shaft 22. In addition, an insulating material 11 with a specific gravity matching that of blood, such as an insulating fluid, may be used to reduce the risk of buoyant forces becoming dominant.

When the insulation material 11 is positioned at the non-contact portion 54 of the electrode 32, the pulsed field ablation generator 14 may be actuated to deliver the pulsed electric field to the electrode 32, such as through the lumen 30. The permeable sheath 38 is configured to directionally focus the pulsed electric field to the focal area 52. For example, when contacting the treatment site 50, the permeable sheath 38 causes the pulsed electric field to flow only from the contact portion 48 of the electrode 32 as the insulation material 11 moves to electrically insulate the non-contact portion 54, which may be in contact with blood. Resultingly, a lesion created at the focal area 52 may be enhanced, the risk of bubbles in the insulation material 11 may be reduced, and/or electroporative effects on the blood may be reduced. The pulsed electric field is configured to generate minimal heating within the treatment site 50, thereby decreasing or eliminating the use of additional electrodes to cool the blood. Accordingly, the electrodes 32 may be configured to contact a surface of the focal area 52 without penetrating relatively deeper into the treatment site 50.

The pulsed electric field provides brief periods of non-thermal therapeutic energy delivery, such as tens of milliseconds in duration. In one exemplary configuration, the pulsed electric field may be delivered by the generator 14 at a frequency less than 3 kHz, such as 1 kHz. In addition, the pulse train of energy may include one or more voltage amplitudes, at least 60 pulses, an inter-phase delay between 0 μs and 5 μs, an inter-pulse delay of at least 400 μs, a pulse width of 1-15 μs, and a voltage between 300V and 4000V.

The pulsed electric field may be timed to coincide with a vulnerable state of the cells within the treatment site 50, which may include a state of maximal length of cardiomyocytes or other myocytes. In addition, because vulnerable tissues not intended to receive ablation may be present in proximity to the treatment site 50, the delivery of the pulsed electrical field may be timed to coincide with the least vulnerable state of such proximate vulnerable tissues. The least vulnerable state may include an assessment of the physical state of the cells within the proximate vulnerable tissues. In the alternative, an energy vectoring scheme may be implemented which has the least effect on the proximate vulnerable tissues by activating or deactivating specific electrodes 32 at the distal portion 28 of the shaft 22.

Figure 5:
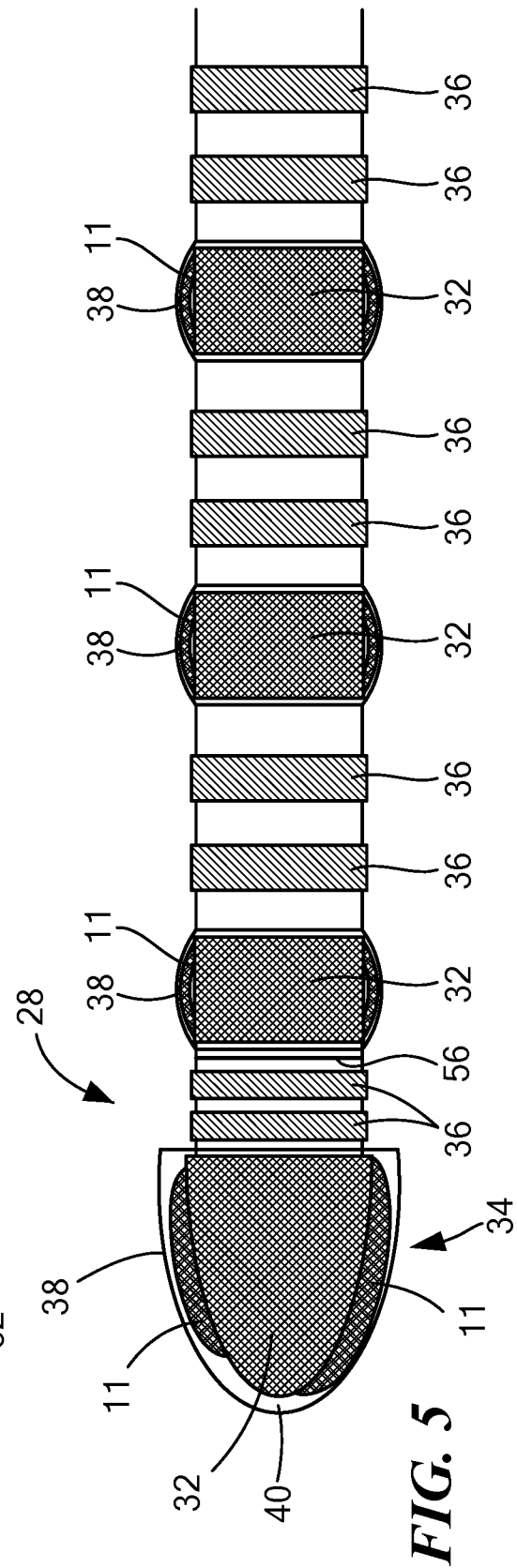
FIG. 5 is a close-up side view that illustrates the shaft of FIG. 1 including a linear configuration having a plurality of electrodes disposed thereon, each surrounded by a permeable sheath.
Figure 6:
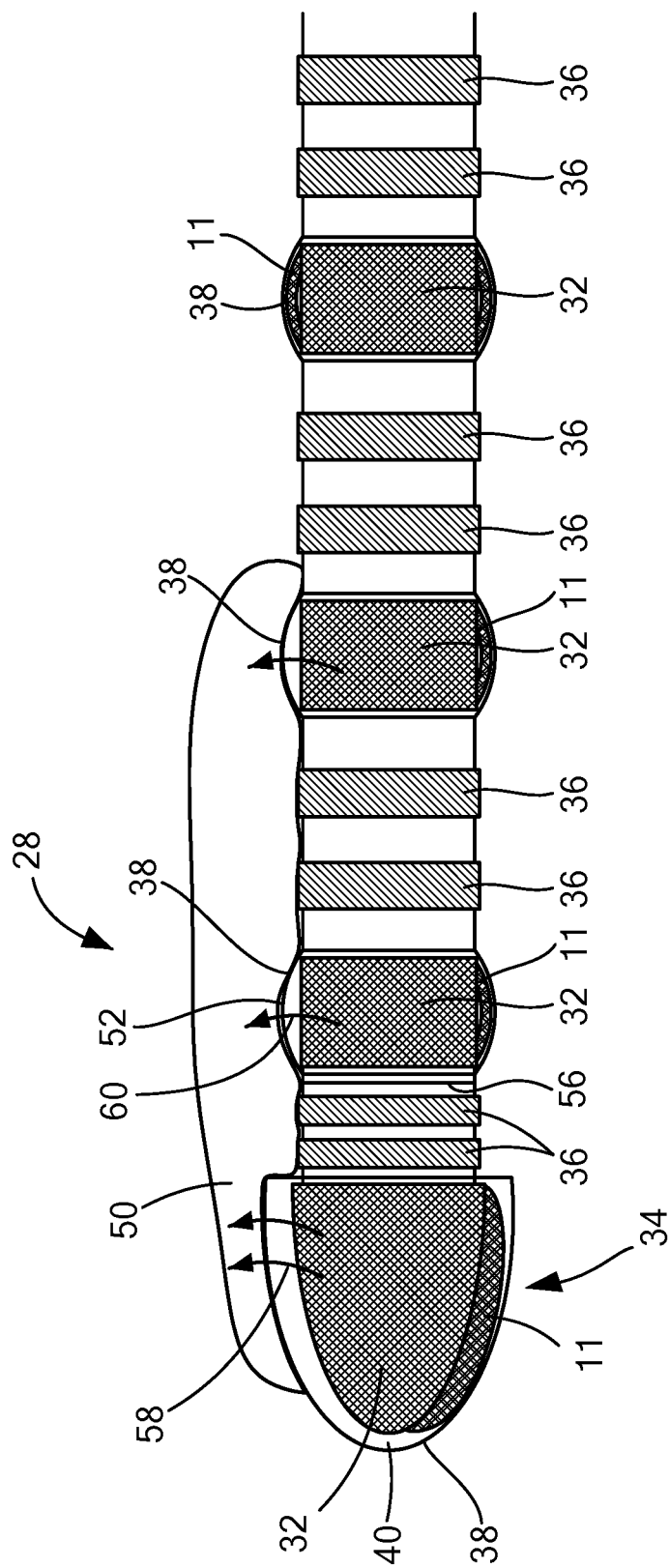
FIG. 6 is a close-up side view that illustrates the shaft of FIG. 5 disposed proximate to a treatment site.

With reference now to FIG. 5, the distal portion 28 of the shaft 22 is depicted without being in contact with the treatment site 50 and having a linear configuration including four electrodes 32 which may be arranged in a unipolar or bipolar energy configuration. In other configurations, more or less electrodes may be included. In one exemplary configuration, a first electrode 32 may be positioned proximate a second electrode 32 and an impermeable membrane 56 may be disposed therebetween to electrically isolate the first electrode 32 and the second electrode 32 from each other to enhance the directional focus of the pulsed electric field. FIG. 6 is a close-up side view that illustrates the distal portion 28 of the shaft 22 in contact with the treatment site 50. The impermeable membrane 56 may also be a separation element that defines a separation distance between a first electric field 58 delivered by the first electrode 32 and a second electric field 60 delivered by the second electrode 32. In another configuration, the separation element may be a super elastic internal element. The pulsed electric field may be delivered to the respective electrodes 32 through wire(s), which may be located within one or more lumens. One or more diagnostic electrodes 36 may be positioned between the electrodes 32. It will be understood that the electrodes 32 may be at locations along the shaft 22 other than those shown in the figures, such as at locations at greater distances proximal from the distal-most end 34 of the shaft 22. It will also be understood that fewer or more electrodes 32 than those shown in FIGS. 5 and 6 may be used. Additionally, the electrode(s) 32 may have a larger surface area than shown in the figures. For example, each electrode 32 may be larger than shown or may include a plurality of smaller electrodes that are electrically connected to each other and function as a single larger electrode.

Figure 7:
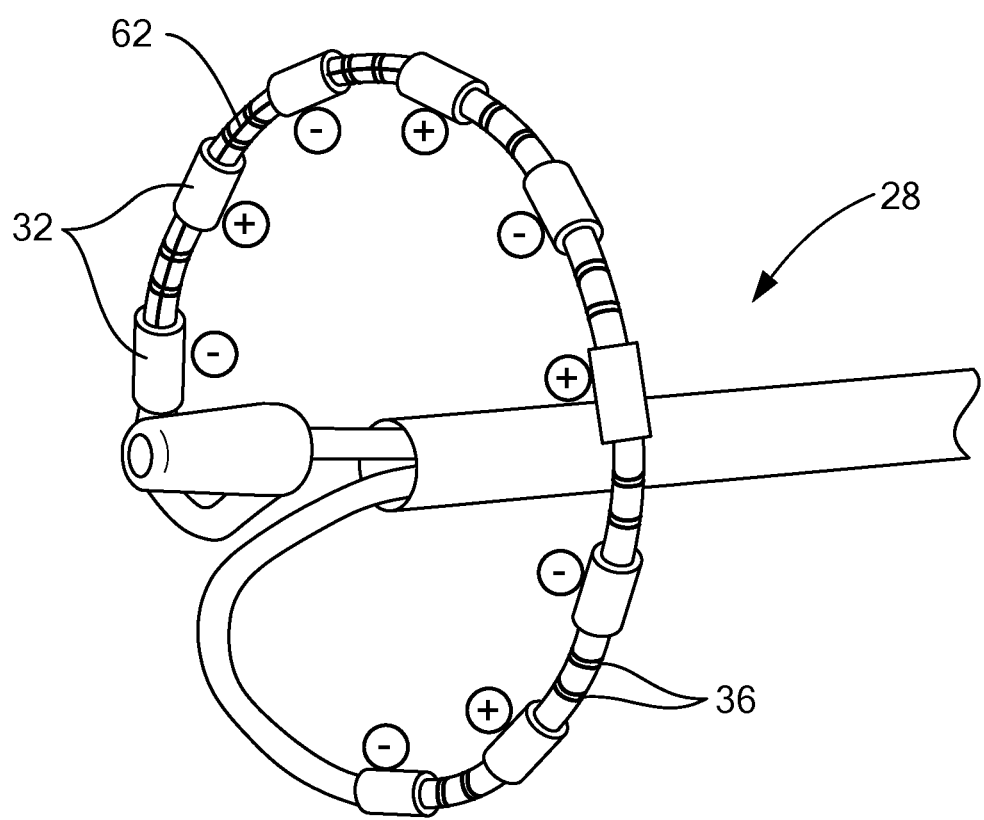
FIG. 7 is a perspective view that illustrates another configuration of a shaft including a circular shape having one or more electrodes disposed thereon.

FIG. 7 is a close-up side view that illustrates the distal portion 28 of the shaft 22 including a flexible member 62 at least partially defining a circular shape of the distal portion 28. For example, the flexible member 62 may be a preformed super elastic wire disposed within the shaft 22. In such configurations, the distal portion 28 may include one or more electrodes 32 arranged in various configurations. For example, a first electrode 32 may be positioned proximate a second electrode 32 with both being energy delivery electrodes. In another configuration, a diagnostic electrode 36 may be positioned proximate the first electrode 32.

In one embodiment, a medical device for directionally focusing energy to a treatment site comprises: a shaft including an elongated body defining a proximal portion and a distal portion opposite the proximal portion, the distal portion including at least one electrode having a contact portion; and a permeable sheath at least partially surrounding the at least one electrode, the permeable sheath being impermeable to an insulation material emitted from a fluid source configured to be coupled to the shaft.

In one aspect of the embodiment, the permeable sheath and the at least one electrode define an insulation cavity therebetween, the insulation cavity being configured to retain the insulation material when the insulation material is emitted from the fluid source.

In one aspect of the embodiment, the permeable sheath is configured to cause energy to flow from the contact portion of the at least one electrode.

In one aspect of the embodiment, the device further comprises a second electrode positioned proximally on the shaft relative to the at least one electrode, the at least one electrode including a conductive surface area smaller than a conductive surface area of the second electrode.

In one aspect of the embodiment, the device further comprises a second electrode proximate the at least one electrode and an impermeable membrane disposed between and electrically isolating the at least one electrode and the second electrode from each other.

In one aspect of the embodiment, the device further comprises a flexible member at least partially defining a circular shape of the distal portion of the elongated body of the shaft, and a second electrode disposed on the distal portion proximate the at least one electrode, the at least one electrode being an energy emitter and the second electrode being a diagnostic electrode.

In one aspect of the embodiment, the device further comprises a second electrode proximate the at least one electrode, and a separation element disposed between the at least one electrode and the second electrode, the separation element defining a separation distance between a first electric field emitted by the at least one electrode and a second electric field emitted by the second electrode.

In one embodiment, a medical system for directionally focusing energy to a treatment site comprises: a medical device including: a shaft having an elongated body defining a proximal portion and a distal portion opposite the proximal portion, the shaft including a plurality of electrodes; and a permeable sheath at least partially surrounding at least one of the plurality of electrodes, the permeable sheath being permeable to a pulsed electric field and impermeable to an insulation material; a fluid source coupled to the medical device for emitting the insulation material; and an energy source coupled to the medical device for emitting the pulsed electric field.

In one aspect of the embodiment, the permeable sheath and at least one electrode of the plurality of electrodes define an insulation cavity therebetween for enclosing the insulation material when emitted by the fluid source. In one aspect of the embodiment, the plurality of electrodes each define an outer surface, and the insulation material is configured to translate from a first position on the outer surface to a second position on the outer surface when the permeable sheath is in contact with the treatment site.

In one aspect of the embodiment, the plurality of electrodes include a first electrode at the distal portion of the shaft and a second electrode positioned proximally on the shaft relative to the first electrode, the first electrode including a conductive surface area smaller than a conductive surface area of the second electrode.

In one aspect of the embodiment, the plurality of electrodes include a first electrode and a second electrode proximate the first electrode and an impermeable membrane disposed between and electrically isolating the first electrode and the second electrode from each other.

In one aspect of the embodiment, the system further comprises a flexible member at least partially defining a circular shape of the distal portion of the shaft, the distal portion of the shaft including a first electrode and a second electrode of the plurality of electrodes disposed thereon, the first electrode being an energy emitter and the second electrode being a diagnostic electrode.

In one aspect of the embodiment, the system further comprises a separation element disposed between the plurality of electrodes, the separation element defining a separation distance between a first electric field and a second electric field emitted by the plurality of electrodes.

In one aspect of the embodiment, the system further comprises a fluid delivery lumen in fluid communication with the fluid source and the permeable sheath.

In one aspect of the embodiment, the system further comprises a fluid circuit in communication with the permeable sheath, the fluid circuit including a fluid delivery lumen and a fluid extraction lumen.

In one embodiment, a method of directionally focusing energy to a treatment site comprises: positioning a distal portion of a medical device adjacent a tissue of a patient, the distal portion including at least one electrode at least partially surrounded by a permeable sheath, the at least one electrode and the permeable sheath defining an insulation cavity, and the permeable sheath being permeable to a pulsed electric field and impermeable to an insulation material; actuating a fluid source to deliver the insulation material from the fluid source to the permeable sheath of the medical device, the insulation material configured to be disposed within the insulation cavity; and actuating an energy source to deliver a pulse field of energy from the energy source to the distal portion of the at least one electrode.

In one aspect of the embodiment, the method further comprises adjusting an amount of the insulation material within the insulation cavity.

In one aspect of the embodiment, the method further comprises positioning the distal portion of the medical device in contact with the tissue.

In one aspect of the embodiment, the method further comprises positioning the distal portion of the medical device in contact with the tissue to transition the insulation material from a first portion of the at least one electrode to a second portion of the at least one electrode.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device for directionally focusing energy to a treatment site comprising:
    a shaft including an elongated body defining a proximal portion and a distal portion opposite the proximal portion, the distal portion including at least one electrode, wherein the at least one electrode is fixedly coupled at a position relative to the shaft;
    a permeable sheath at least partially surrounding the at least one electrode, the permeable sheath being impermeable to an insulation material and permeable to a pulsed electric field, the permeable sheath and the at least one electrode defining an insulation cavity therebetween;
    the at least one electrode being configured to deliver a pulsed electric field; and
    the insulation material being a displaceable material that fills a portion of the insulation cavity, wherein the insulation material is configured to translate relative to a surface of the at least one electrode in response to contact between the permeable sheath and a treatment site such that the insulation material is in contact with only a non-contact portion of the at least one electrode and energy of the delivered pulsed electric field is directed only through the a contact portion of the at least one electrode.

2. The medical device according to claim 1, wherein the permeable sheath is composed of a hydrophilic permeable membrane and the insulation material is at least one of a gas and a hydrophobic material such that the insulation material is retained within the hydrophilic permeable membrane.

3. The medical device according to claim 1, wherein the insulation material is introduced into the insulation cavity from a fluid source configured to be coupled to the shaft, the insulation cavity being configured to retain the insulation material when the insulation material is introduced into the insulation cavity from the fluid source.

4. The medical device according to claim 1, wherein the insulation material is a displaceable solid material.

5. The medical device according to claim 4, wherein the displaceable solid material is at least one of granular particles, microspheres, ceramic microspheres, polymeric microspheres, and hydrophobic polymeric microspheres, the insulation cavity containing a predetermined amount of the insulation material.

6. The medical device according to claim 1, wherein the permeable sheath is configured to cause the energy to flow from the contact portion of the at least one electrode.

7. The medical device according to claim 1, further comprising a second electrode positioned proximally on the shaft relative to the at least one electrode, the at least one electrode including a conductive surface area smaller than a conductive surface area of the second electrode.

8. The medical device according to claim 1, further comprising a second electrode proximate the at least one electrode and an impermeable membrane disposed between and electrically isolating the at least one electrode and the second electrode from each other.

9. The medical device according to claim 1, further comprising a second electrode proximate the at least one electrode, and a separation element disposed between the at least one electrode and the second electrode, the separation element defining a separation distance between a first electric field delivered by the at least one electrode and a second electric field delivered by the second electrode.

10. A medical system for directionally focusing energy to a treatment site comprising:
    a medical device including:
        a shaft having an elongated body defining a proximal portion and a distal portion opposite the proximal portion, the shaft including a plurality of electrodes, wherein at least one electrode of the plurality of electrodes is fixedly coupled at a position relative to the shaft; and
        a permeable sheath at least partially surrounding the at least one electrode of the plurality of electrodes, the permeable sheath being permeable to a pulsed electric field and impermeable to an insulation material, the permeable sheath and the at least one electrode of the plurality of electrodes defining an insulation cavity therebetween for enclosing the insulation material;
        the at least one electrode of the plurality of electrodes being configured to deliver a pulsed electric field; and
        the insulation material being a displaceable material that fills a portion of the insulation cavity, wherein the insulation material is configured to translate relative to a surface of the at least one electrode in response to contact between the permeable sheath and a treatment site such that the insulation material is in contact with only a non-contact portion of the at least one of the plurality of electrodes and energy of the delivered pulsed electric field is directed only through a contact portion of the at least one of the plurality of electrodes;
    a fluid source coupled to the medical device, the fluid source being configured to introduce the insulation material into the insulation cavity; and an energy source coupled to the medical device, the energy source being configured to transmit the pulsed electric field to the at least one electrode of the plurality of electrodes.

11. The medical system according to claim 10, wherein the plurality of electrodes includes a first electrode at the distal portion of the shaft and a second electrode positioned proximally on the shaft relative to the first electrode, the first electrode including a conductive surface area smaller than a conductive surface area of the second electrode.

12. The medical system according to claim 10, wherein the plurality of electrodes includes a first electrode and a second electrode proximate the first electrode and an impermeable membrane disposed between and electrically isolating the first electrode and the second electrode from each other.

13. The medical system according to claim 10, wherein the medical device further includes a separation element disposed between the plurality of electrodes, the separation element defining a separation distance between a first electric field and a second electric field delivered by the plurality of electrodes.

14. The medical system according to claim 10, wherein the medical device further includes a fluid delivery lumen in fluid communication with the fluid source and the insulation cavity.

15. The medical system according to claim 10, further comprising a fluid circuit in communication with the insulation cavity, the fluid circuit including a fluid delivery lumen and a fluid extraction lumen.

16. The medical device according to claim 1, wherein:
the medical device is transitionable between a first configuration and a second configuration different than the first configuration;
when in the first configuration, the insulation material surrounds an entirety of the at least one electrode; and
when in the second configuration, the insulation material surrounds only the non-contact portion of the at least one electrode.

17. The medical system according to claim 10, wherein:
the medical device is transitionable between a first configuration and a second configuration different than the first configuration;
when in the first configuration, the insulation material surrounds an entirety of the at least one electrode; and
when in the second configuration, the insulation material surrounds only the non-contact portion of the at least one electrode.

18. The medical device according to claim 1, wherein the insulation material is an electrically insulating material, and wherein the at least one electrode includes at least one selected from a group consisting of a rigid curvilinear surface and a rigid semi-ellipsoidal surface.

19. The medical system according to claim 10, wherein the insulation material is an electrically insulating material, and wherein the at least one electrode of the plurality of electrodes includes at least one selected from a group consisting of a rigid curvilinear surface and a rigid semi-ellipsoidal surface.

* * * * *